US012067655B2

(12) United States Patent
Tanabe et al.

(10) Patent No.: US 12,067,655 B2
(45) Date of Patent: Aug. 20, 2024

(54) IMAGE PROCESSING METHOD, IMAGE PROCESSING DEVICE AND PROGRAM MEMORY MEDIUM

(71) Applicant: NIKON CORPORATION, Tokyo (JP)

(72) Inventors: Yasushi Tanabe, Fujisawa (JP); Daishi Tanaka, Konosu (JP); Makoto Ishida, Ageo (JP); Mariko Mukai, Yokohama (JP)

(73) Assignee: NIKON CORPORATION, Tokyo (JP)

( * ) Notice: Subject to any disclaimer, the term of this patent is extended or adjusted under 35 U.S.C. 154(b) by 32 days.

(21) Appl. No.: 17/576,054

(22) Filed: Jan. 14, 2022

(65) Prior Publication Data

US 2022/0230371 A1    Jul. 21, 2022

(30) Foreign Application Priority Data

Jan. 15, 2021   (JP) .................................. 2021-005188

(51) Int. Cl.
| | |
|---|---|
| *G06T 11/60* | (2006.01) |
| *A61B 3/10* | (2006.01) |
| *A61B 3/12* | (2006.01) |
| *A61B 5/00* | (2006.01) |
| *G06T 19/00* | (2011.01) |

(52) U.S. Cl.
CPC .............. *G06T 11/60* (2013.01); *A61B 3/102* (2013.01); *A61B 3/12* (2013.01); *A61B 5/0035* (2013.01); *A61B 5/004* (2013.01); *G06T 19/00* (2013.01); *G06T 2210/41* (2013.01)

(58) Field of Classification Search
None
See application file for complete search history.

(56) References Cited

U.S. PATENT DOCUMENTS

| | | | |
|---|---|---|---|
| 2012/0083667 A1 | 4/2012 | Isogai et al. | |
| 2015/0094566 A1* | 4/2015 | Ryu ....................... | A61B 5/489 |
| | | | 600/424 |
| 2018/0064332 A1* | 3/2018 | Filippatos .............. | A61B 90/20 |
| 2018/0153396 A1* | 6/2018 | Uchida .................. | A61B 3/102 |
| 2018/0344154 A1* | 12/2018 | Svetliza ............... | A61B 3/1208 |

(Continued)

FOREIGN PATENT DOCUMENTS

JP    2018-075229 A    5/2018

OTHER PUBLICATIONS

Ahdi et al. (A hybrid method for 3D mosaicing of OCT images of macula and Optic Nerve Head, computers in Biology and Medicine, 2017) (Year: 2017).*

(Continued)

*Primary Examiner* — Kyle Zhai
(74) *Attorney, Agent, or Firm* — FOLEY & LARDNER LLP

(57) ABSTRACT

An image processing method includes acquiring a three-dimensional image of a subject eye and a two-dimensional image of the subject eye, specifying a first reference point in the three-dimensional image, specifying a second reference point in the two-dimensional image, and generating a superposed image. In the superposed image, the first reference point in the three-dimensional image is coordinated with the second reference point in the two-dimensional image and the two-dimensional image is superposed with at least a portion of the three-dimensional image.

19 Claims, 13 Drawing Sheets

(56) References Cited

U.S. PATENT DOCUMENTS

2022/0095909 A1* 3/2022 Charles .................. A61B 3/102
2023/0172449 A1* 6/2023 Lefaudeux ............. A61B 3/152
                                                       351/206

OTHER PUBLICATIONS

Matsumoto et al. (Quantitative measures of vortex veins in the posterior pole in eyes with pachychoroid spectrum diseases, Scientific reports, 2020) (Year: 2020).*

Han et al. (Three Dimensional Simulation for Blood Vessel of Ocular Fundus, IEEE, 2009) (Year: 2009).*

Moriyama et al. (Topographic Analyses of Shape of Eyes with Pathologic Myopia by High-Resolution Three-Dimensional Magnetic Resonance Imaging, American Academy Ophthalmology, 2011) (Year: 2011).*

Japanese Office Action in Japanese Application No. 2021-005188 dated Jun. 4, 2024 (4 pages).

* cited by examiner

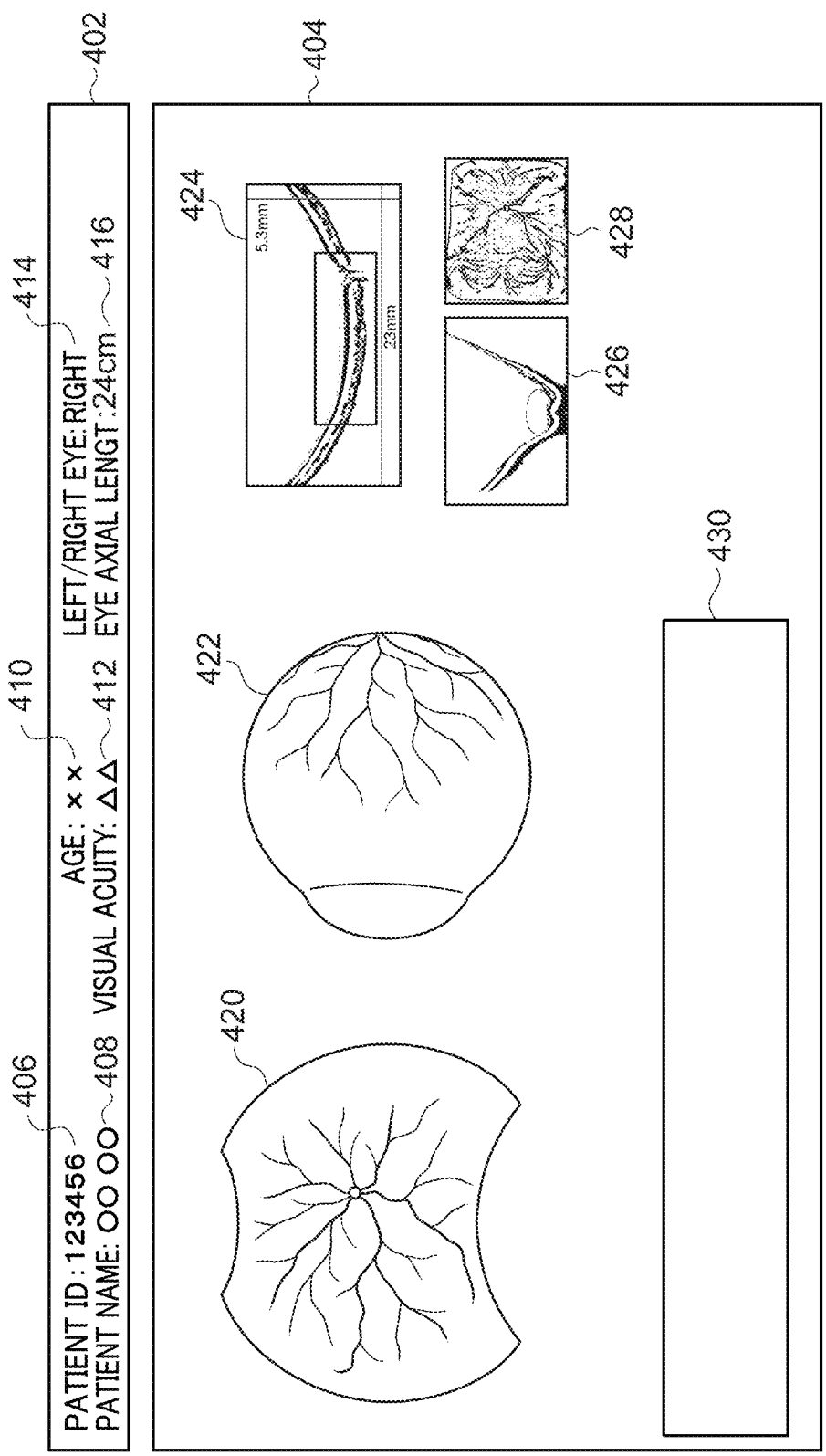

IMAGE PROCESSING METHOD, IMAGE PROCESSING DEVICE AND PROGRAM MEMORY MEDIUM

CROSS-REFERENCE TO RELATED APPLICATIONS

This application claims priority from Japanese Patent Application No. 2021-005188, filed on Jan. 15, 2021, the disclosures of which are incorporated by reference herein in their entirety.

BACKGROUND

Field of the Invention

The technology of the present disclosure relates to an image processing method, an image processing device and a program.

Related Art

Construction of eyeball models from magnetic resonance imaging (MM) images is known (International Publication No. 2013-031536).

SUMMARY

An image processing method according to a first aspect of the technology of the present disclosure includes: acquiring a three-dimensional image of a subject eye and a two-dimensional image of the subject eye; specifying a first reference point in the three-dimensional image; specifying a second reference point in the two-dimensional image; and generating an image in which the two-dimensional image is superposed with at least a portion of the three-dimensional image, including coordinating the first reference point in the three-dimensional image with the second reference point in the two-dimensional image.

An image processing device according to a second aspect of the technology of the present disclosure includes memory and a processor connected to the memory, the processor executing an image processing method including: acquiring a three-dimensional image of a subject eye and a two-dimensional image of the subject eye; specifying a first reference point in the three-dimensional image; specifying a second reference point in the two-dimensional image; and generating an image in which the two-dimensional image is superposed with at least a portion of the three-dimensional image, including coordinating the first reference point in the three-dimensional image with the second reference point in the two-dimensional image.

A non-transitory memory medium according to a third aspect of the technology of the present disclosure memorizes a program executable by a computer to execute image processing including: acquiring a three-dimensional image of a subject eye and a two-dimensional image of the subject eye; specifying a first reference point in the three-dimensional image; specifying a second reference point in the two-dimensional image; and generating an image in which the two-dimensional image is superposed with at least a portion of the three-dimensional image, including coordinating the first reference point in the three-dimensional image with the second reference point in the two-dimensional image.

An image processing method according to a fourth aspect of the technology of the present disclosure includes: acquiring a first image that is a three-dimensional image imaging a subject eye in a first modality; acquiring a second image imaging the subject eye in a second modality that is different from the first modality; specifying a first structural feature in the first image; specifying a second structural feature in the second image, the second structural feature corresponding with the first structural feature; and generating an image in which at least a portion of the second image is superposed with at least a portion of the first image by reference to the first structural feature and the second structural feature.

BRIEF DESCRIPTION OF THE DRAWINGS

FIG. 14 is a view depicting a display screen 400.

DETAILED DESCRIPTION

Below, exemplary embodiments of the technology of the present disclosure are described in detail with reference to the attached drawings.

Figure 1:
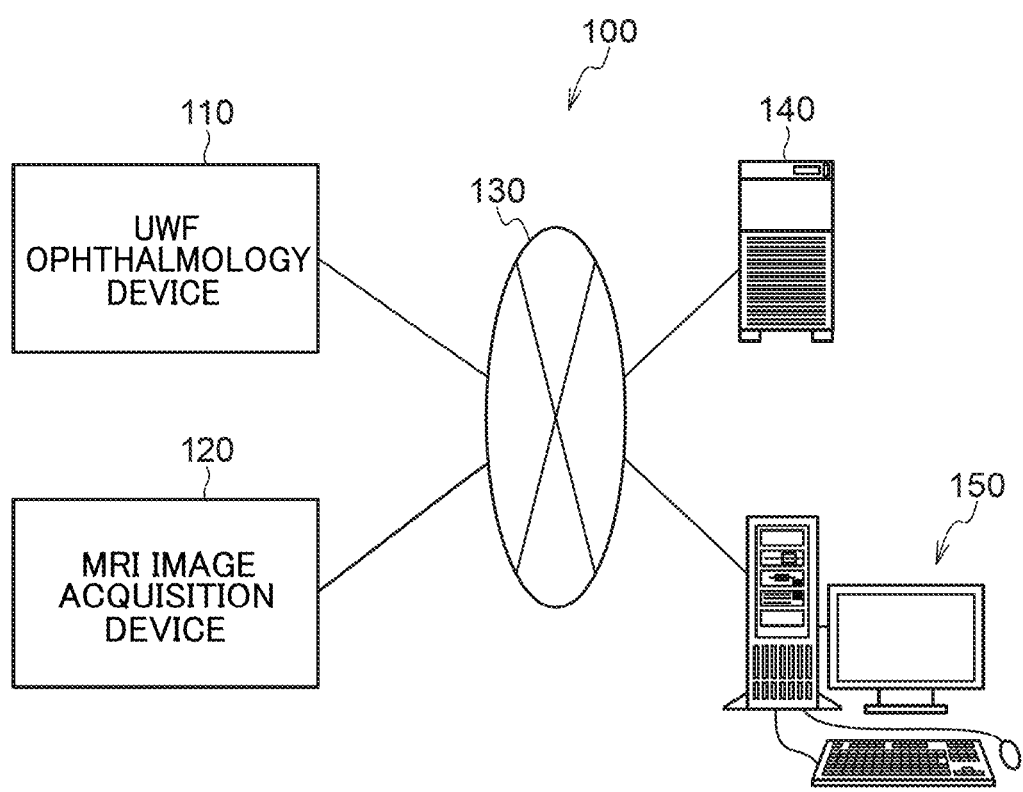
FIG. 1 is a block diagram showing structures of an ophthalmology system 100 according to a present exemplary embodiment.

Structures of an ophthalmology system 100 according to the exemplary embodiment of the technology of the present disclosure are described with reference to FIG. 1. FIG. 1 is a block diagram showing the structures of the ophthalmology system 100 according to the present exemplary embodiment. As shown in FIG. 1, the ophthalmology system 100 is provided with an ultra-wide field (UWF) ophthalmology device 110, an MRI image acquisition device 120, a network 130, a management server device (below referred to as the management server) 140, and an image display device (below referred to as the image viewer) 150.

The UWF ophthalmology device 110, MRI image acquisition device 120, management server 140 and image viewer 150 are connected to one another via the network 130. The network 130 is an arbitrary network such as a LAN, a WAN, the Internet, a wide area Ethernet or the like. For example, when the ophthalmology system 100 is constituted in a single hospital, a LAN may be employed for the network 130.

The MRI image acquisition device 120 is a device at which a subject eye is disposed in a strong static magnetic field (produced by superconduction, ordinary conduction or a permanent magnet) and electromagnetic waves are applied to the subject eye in any of various pulse sequences, after which nuclear magnetic resonance imaging is applied, and biochemical information of hydrogen atom nuclei is processed as signals and converted to an image (see Non-Patent Reference 1). The image constituting factors are relaxation times T and T2 and hydrogen nuclei densities. By selecting a suitable pulse sequence, an image in which the relaxation times T1 and T2, hydrogen nuclei densities or the like are emphasized can be obtained (an MRI three-dimensional eyeball image). Pulse sequences that may be employed include a saturation recovery (SR) sequence, an inversion recovery (IR) sequence, a spin echo (SE) sequence, a STIR sequence and so forth. An MRI three-dimensional eyeball image obtained by the MRI image acquisition device 120 is a surface image (a spherical surface image) obtained by modelling a three-dimensional shape. The MRI three-dimensional eyeball image includes each of structural parts such as the eyeball and the optic nerve.

Non-Patent Reference 1: NAKAO Yuzo, MRI Examination in Ophthalmology, p. 1 [online], Japan Association of Certified Orthoptists, Fifth lecture meeting, Internet: <https://www.jstage.jst.go.jp/article/jorthoptic1977/18/0/18_0_1/_pdf/-char/ja>

The UWF ophthalmology device 110 images funduses and obtains various UWF fundus images and optical coherence tomography (OCT) images, which are described below. The MRI image acquisition device 120 acquires MRI three-dimensional eyeball images of subject eyes. The management server 140 receives the UWF fundus images, optical OCT images and MRI three-dimensional eyeball images through the network 130 in association with patient IDs, and stores the images in a memory 164 (see FIG. 3). Thus, various UWF fundus images, OCT images and MRI three-dimensional eyeball images are memorized in the memory 164 of the management server 140 in association with the patient IDs of the respective patients. The management server 140 transmits various images through the network 130 to the image viewer 150.

The image viewer 150 includes a touch panel, a display and the like and features communication functions. The image viewer 150 displays fundus images acquired by the management server 140.

Other ophthalmological equipment (test devices for field of vision measurement, intraocular pressure measurement and the like), diagnostics support devices that use artificial intelligence for image analysis and so forth may be connected to the UWF ophthalmology device 110, MRI image acquisition device 120, management server 140 and image viewer 150 via the network 130.

Figure 2:
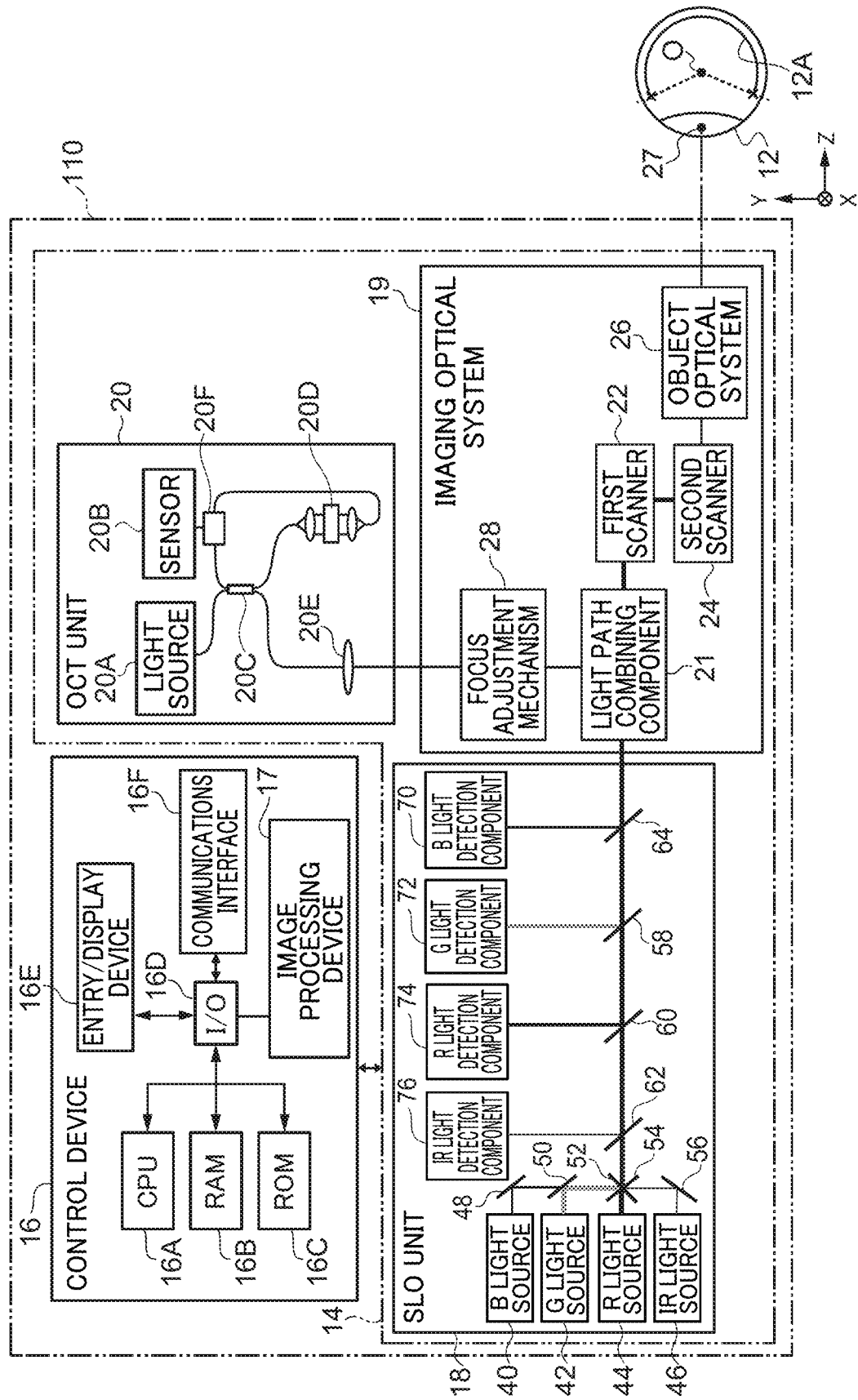
FIG. 2 is a block diagram showing structures of an electronic system of a UWF ophthalmology device 110.

Now, structures of the UWF ophthalmology device 110 are described with reference to FIG. 2. FIG. 2 is a block diagram showing hardware structures of the UWF ophthalmology device 110 according to the present exemplary embodiment. As shown in FIG. 2, the UWF ophthalmology device 110 includes an imaging device 14 and a control device 16.

When the UWF ophthalmology device 110 is placed on a flat surface, a horizontal direction serves as an X direction, a vertical direction relative to the horizontal direction serves as a Y direction, and an optical axis direction of an imaging optical system 19 serves as a Z direction. The device is disposed relative to a subject eye 12 such that the center of a pupil 27 of the subject eye is disposed on the optical axis of the Z direction. The X direction, Y direction and Z direction are mutually perpendicular.

The control device 16 is provided with a computer including a central processing unit (CPU) 16A, random access memory (RAM) 16B, read-only memory (ROM) 16C, an input/output (I/O) port 16D, an entry/display device 16E, and a communications interface (I/F) 16F. The structures of the control device 16 are connected to be capable of communicating with one another via a bus.

The CPU 16A is a central arithmetic processing unit, which executes various programs and controls various sections. That is, the CPU 16A reads a program from the ROM 16C and executes the program using the RAM 16B as a work area. The CPU 16A performs control of respective structures and arithmetic processing in accordance with the program memorized in the ROM 16C. In the present exemplary embodiment, a scanning program for executing scanning processing is memorized in the ROM 16C.

The RAM 16B serves as a work area and temporarily memorizes programs and data. The ROM 16C memorizes various programs and data. The control device 16 may also be provided with storage constituted by a memory device such as a hard disk drive (HDD), a solid state drive (SSD) or the like, in which case various programs, including an operating system, and various kinds of data are memorized in the storage.

The entry/display device 16E is connected to the CPU 16A via the I/O port 16D. The entry/display device 16E includes a graphical user interface (GUI) that displays images of the subject eye 12 and accepts various instructions from a user. A touch panel and display or the like may be employed as the GUI. The control device 16 is further provided with an image processing device 17 connected to the I/O port 16D.

The control device 16 is connected to the network 130 via the communications interface 16F. The communications interface 16F is an interface for communications with other equipment. The communications interface 16F employs a standard such as, for example, Ethernet (registered trademark), FDDI, Wi-Fi (registered trademark) or the like.

In FIG. 2, the control device 16 of the UWF ophthalmology device 110 is provided with the entry/display device 16E, but the technology of the present disclosure is not limited thus. For example, rather than the control device 16 of the UWF ophthalmology device 110 being provided with the entry/display device 16E, a separate entry/display device that is physically separate from the UWF ophthalmology device 110 may be provided. In this case, the display device is provided with an image processing processor unit that operates under the control of the CPU 16A of the control device 16. The image processing processor unit may display acquired images and the like on the basis of image signals whose output is commanded by the CPU 16A.

The image processing device 17 generates images of the subject eye 12 on the basis of data obtained by the imaging device 14. The image processing device 17 may be omitted and the CPU 16A may generate images of the subject eye 12 on the basis of data obtained by the imaging device 14.

The imaging device 14 captures images of the subject eye 12. The imaging device 14 operates under the control of the control device 16. For convenience of description, a scanning laser ophthalmoscope is referred to as an SLO. The imaging device 14 includes the imaging optical system 19, an SLO unit 18 and an OCT unit 20. The SLO unit 18 acquires an image of a fundus 12A of the subject eye 12. The OCT unit 20 acquires a tomographic image of the subject eye 12.

Below, an elevation view image of a retina that is created on the basis of SLO data obtained by the SLO unit 18 is referred to as an SLO image. A tomographic image, an elevation image (en-face image) or the like of the retina that is created on the basis of OCT data acquired by the OCT unit 20 is referred to as an OCT image. An SLO image is mentioned as a two-dimensional fundus image. An OCT image is mentioned as a fundus tomographic image or an anterior eye part tomographic image, depending on an imaged region of the subject eye 12.

The imaging optical system 19 is moved in the X, Y, and Z directions by an imaging optical system driving section, which is not shown in the drawings, under the control of the CPU 16A. Alignment (positioning) of the imaging device 14 and the subject eye 12 may be implemented by, for example, moving the whole of the UWF ophthalmology device 110 in the X, Y and Z directions rather than only the imaging device 14.

The imaging optical system 19 includes a light path combining component 21, a first scanner 22, a second scanner 24, and an object optical system 26. The light path combining component 21 is a half mirror or a beam splitter. The first scanner 22 and the second scanner 24 are optical scanners.

The object optical system 26 may be a reflecting optical system using a concave mirror such as an elliptical mirror or the like, a refracting optical system using a wide-angle lens or the like, or a reflecting and refracting optical system combining a concave mirror with a lens or the like. When a wide-angle optical system using an elliptical mirror and a wide-angle lens or the like is employed, areas of the retina around the fundus may be imaged rather than just a central fundus area.

When a system including an elliptical mirror is employed, the system using an elliptical mirror may be configured as recited in International Publication No. WO2016/103484 or WO2016/103489. The respective disclosures of International Publication Nos. WO2016/103484 and WO2016/103489 are incorporated into the present specification by reference in their entirety.

Observation of the fundus in a wide field of view (FOV) is realized by the imaging optical system 19. The FOV represents a range that can be imaged by the imaging device 14. The FOV may be expressed as a viewing angle. A viewing angle in the present exemplary embodiment may be specified as an internal illumination angle and an external illumination angle. The external illumination angle is an illumination angle of light flux illuminated from the UWF ophthalmology device 110 toward the subject eye that is specified by reference to the pupil. The internal viewing angle is an illumination angle of light flux illuminated toward the fundus 12A that is specified by reference to an eyeball center O. The external illumination angle and internal illumination angle have a correspondence relationship. For example, when the external illumination angle is 120°, the internal illumination angle is around 160°. In the present exemplary embodiment, the internal illumination angle is 200°.

An SLO fundus image that is obtained by imaging with an internal illumination angle of 160° or more as an imaging field of view is referred to as a UWF-SLO fundus image.

First, SLO image acquisition is described.

The SLO unit 18 is equipped with plural light sources. As shown in FIG. 2, the SLO unit 18 is provided with a B (blue light) light source 40, a G (green light) light source 42, an R (red light) light source 44, and an IR (infrared radiation (for example, near-infrared light)) light source 46. The SLO unit 18 is also provided with optical systems 48, 50, 52, 54 and 56 that reflect or transmit to guide the lights emitted from the light sources 40, 42, 44, and 46 to a single light path. The optical systems 48, 50 and 56 are mirrors and the optical systems 52 and 54 are beam splitters. The B light is reflected at the optical system 48, transmitted through the optical system 50 and reflected by the optical system 54. The G light is reflected by the optical systems 50 and 54. The R light is transmitted through the optical systems 52 and 54. The IR light is reflected by the optical systems 52 and 56. Thus, the respective lights are guided to the single light path.

LED light sources, laser light sources or the like may be employed as the light sources 40, 42, 44, and 46. Below, an example in which laser light sources are employed is described. Full-reflecting mirrors may be employed as the optical systems 48 and 56. Dichroic mirrors, half-mirrors or the like may be employed as the optical systems 50, 52 and 54.

The SLO unit 18 is configured to be capable of switching between various light emission modes, such as light emission modes in which the G light, R light, B light and IR light are respectively individually emitted and light emission modes in which all the lights or some of the lights are emitted at the same time. In the example illustrated in FIG. 2, four light sources are provided—the B (blue light) light source 40, the G light source 42, the R light source 44 and the IR light source 46—but the technology of the present disclosure is not limited thus. For example, the SLO unit 18 may be further provided with a white light light source, in which case a light emission mode that emits only white light and suchlike may be specified in addition to the various light emission modes mentioned above.

Laser light from the SLO unit 18 that enters the imaging optical system 19 is scanned in the X direction and the Y direction by the first scanner 22 and second scanner 24 of the imaging optical system 19. The scanned light passes through the pupil 27 and is illuminated onto a posterior eye part of the subject eye 12 (for example, the fundus 12A). Reflected light that is reflected by the fundus 12A passes back through the imaging optical system 19 and enters the SLO unit 18.

The reflected light that is reflected by the fundus 12A is detected by light detection components 70, 72, 74 and 76 that are provided in the SLO unit 18. In the present exemplary embodiment, the SLO unit 18 is equipped with a B light detection component 70, a G light detection component 72, an R light detection component 74 and an IR light detection component 76 corresponding with the plural light sources, that is, the B light source 40, the G light source 42, the R light source 44 and the IR light source 46. The B light detection component 70 detects B light, which is reflected by a beam splitter 64. The G light detection component 72 detects G light, which is transmitted through the beam splitter 64 and reflected by a beam splitter 58. The R light detection component 74 detects R light, which is transmitted through the beam splitters 64 and 58 and reflected by a beam splitter 60. The IR light detection component 76 detects IR light, which is transmitted through the beam splitters 64, 58 and 60 and reflected by a beam splitter 62. The light detection components 70, 72, 74 and 76 may be, for example, avalanche photodiodes (APD).

Under the control of the CPU 16A, the image processing device 17 uses respective signals detected by the B light detection component 70, the G light detection component 72, the R light detection component 74 and the IR light detection component 76 to generate SLO images corresponding to the respective colors. The SLO images corresponding to the respective colors are a B-SLO image that is generated using the signals detected by the B light detection component 70, a G-SLO image that is generated using the signals detected by the G light detection component 72, an R-SLO image that is generated using the signals detected by the R light detection component 74, and an IR-SLO image that is generated using the signals detected by the IR light detection component 76. In a light emission mode in which the B light source 40, the G light source 42 and the R light source 44 emit light at the same time, an RGB-SLO image is combined from a B-SLO image, G-SLO image and R-SLO image generated using the respective signals detected by the R light detection component 74, the G light detection component 72 and the B light detection component 70. In a light emission mode in which the G light source 42 and the R light source 44 emit light at the same time, an RG-SLO image is combined from a G-SLO image and R-SLO image generated using the respective signals detected by the R light detection component 74 and the G light detection component 72.

Dichroic mirrors, half-mirrors or the like may be employed for the beam splitters 58, 60, 62 and 64.

Now, OCT image acquisition is described. The OCT system is a three-dimensional image acquisition device realized by the control device 16, the OCT unit 20 and the imaging optical system 19 shown in FIG. 2. The OCT unit 20 includes a light source 20A, a sensor (detection component) 20B, a first light coupler 20C, a reference light optical system 20D, a collimator lens 20E, and a second light coupler 20F.

The light source 20A generates light for light interference tomographic imaging. The light source 20A that is employed may be, for example, a super luminescent diode (SLD). The light source 20A generates low-interference light from a broadband light source with a wide spectral width. The light emitted from the light source 20A is divided at the first light coupler 20C. One of the divided lights serves as measurement light, is made parallel by the collimator lens 20E and enters the imaging optical system 19. The measurement light is scanned in the X direction and the Y direction by the first scanner 22 and second scanner 24 of the imaging optical system 19. The scanned light is illuminated onto a posterior eye part via an anterior eye part and the pupil 27. Measurement light that is reflected by the anterior eye part or the posterior eye part passes through the imaging optical system 19 and enters the OCT unit 20, and enters the second light coupler 20F via the collimator lens 20E and the first light coupler 20C. In the present exemplary embodiment, an SD-OCT employing an SLD is illustrated as the light source 20A, but this is not limiting. An SS-OCT employing a wavelength-sweeping light source instead of the SLD may be employed.

The other light that is emitted from the light source 20A and split at the first light coupler 20C serves as reference light, is incident on the reference light optical system 20D, and passes through the reference light optical system 20D and enters the second light coupler 20F.

The measurement light that is reflected and scattered by the subject eye 12 (returning light) combines with the reference light in the second light coupler 20F and produces interference light. The interference light is detected by the sensor 20B. On the basis of detection signals (OCT data) from the sensor 20B, the image processing device 17 generates a tomographic image of the subject eye 12.

The OCT system generates a tomographic image of the anterior eye part or the posterior eye part of the subject eye 12.

The anterior eye part of the subject eye 12 is a region serving as an anterior eye segment including, for example, the cornea, iris, corner angle, crystalline lens, ciliary body and a portion of the vitreous body. The posterior eye part of the subject eye 12 is a region serving as a posterior eye segment including, for example, the remaining portion of the vitreous body and the retina, choroid and sclera. The vitreous body belonging to the anterior eye part is a region at the cornea side of the interior of the vitreous body that is bounded by an X-Y plane passing through a point of the crystalline lens that is closest to the eyeball center. The vitreous body belonging to the posterior eye part is the region of the interior of the vitreous body that is excluded from the vitreous body belonging to the anterior eye part.

When a region to be imaged is the anterior eye part of the subject eye 12, the OCT system generates a tomographic image of, for example, the cornea. When a region to be imaged is the posterior eye part of the subject eye 12, the OCT system generates a tomographic image of, for example, the retina. Below, a tomographic image of the cornea is referred to as an anterior eye part OCT image, and a tomographic image of the retina is referred to as a posterior eye part OCT image. An OCT image including an anterior eye part OCT image and a posterior eye part OCT image is referred to as a whole-eye OCT image (an OCT image of the whole subject eye).

Light that is emitted from the OCT unit 20 and passes through the light path combining component 21 is scanned in the X direction by the first scanner 22. The second scanner 24 scans the light emitted from the OCT unit 20 in the Y direction. It is sufficient that the first scanner 22 and second scanner 24 are optical components that are capable of deflecting light flux; for example, a polygon mirror, a galvano mirror or the like may be employed. Combinations of these components may be used. The first scanner 22 and the second scanner 24 may be structured as a single optical scanner.

The object optical system 26 is an optical system that guides the light guided by the first scanner 22 and second scanner 24 to the subject eye 12. The object optical system 26 may be a reflecting optical system using a concave mirror such as an elliptical mirror or the like, a refracting optical system using a wide-angle lens or the like, or a reflecting and refracting optical system combining a concave mirror with a lens or the like. When a wide-angle optical system using an elliptical mirror and a wide-angle lens or the like is employed, areas of the retina around the fundus may be imaged rather than just a central fundus area.

A focus adjustment mechanism 28 is provided that adjusts the focus of the measurement light from the OCT unit 20. The focus adjustment mechanism 28 is a single optical adjustment mechanism, which is described below.

The light emitted from the light source 20A is split by the first light coupler 20C. One of the split lights serves as the measurement light, is made parallel by the collimator lens 20E, and subsequently enters the imaging optical system 19. The measurement light is scanned in the X direction and the Y direction by the first scanner 22 and second scanner 24. The scanned light passes through the object optical system 26 and pupil 27 and is illuminated onto the fundus. Measurement light that is reflected by the fundus passes through the object optical system 26, the second scanner 24 and the first scanner 22 and enters the OCT unit 20, and then passes through the collimator lens 20E and the first light coupler 20C and enters the second light coupler 20F.

The other light that is emitted from the light source 20A and split at the first light coupler 20C serves as the reference light, enters the reference light optical system 20D, and passes through the reference light optical system 20D and enters the second light coupler 20F. The lights entering the second light coupler 20F, which is to say the measurement light reflected from the fundus and the reference light, interfere in the second light coupler 20F and produce interference light. The interference light is sensed by the sensor 20B. The image processing device 17, operating under the control of an image processing section 182 (see FIG. 5), generates an OCT image on the basis of OCT data detected by the sensor 20B, such as a tomographic image, an en-face image or the like.

Figure 3:
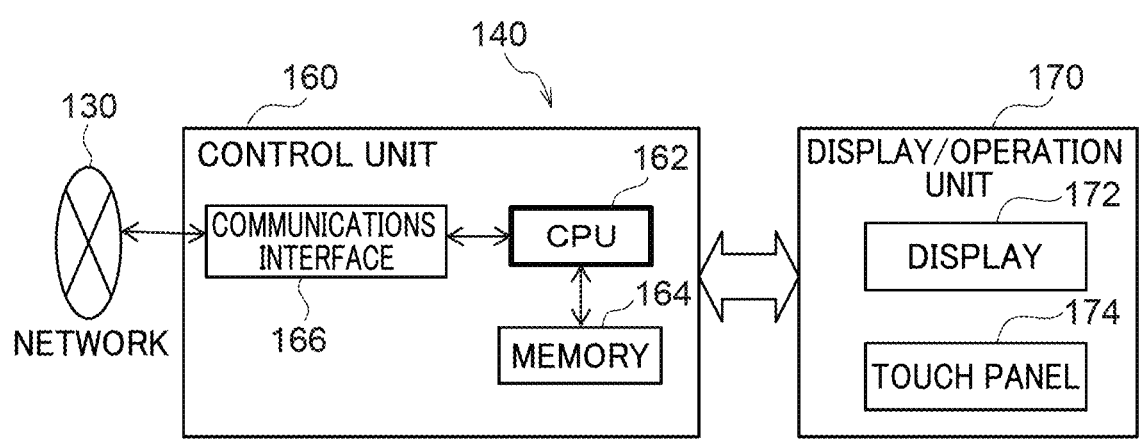
FIG. 3 is a block diagram showing structures of an electronic system of a management server 140.
Figure 6:
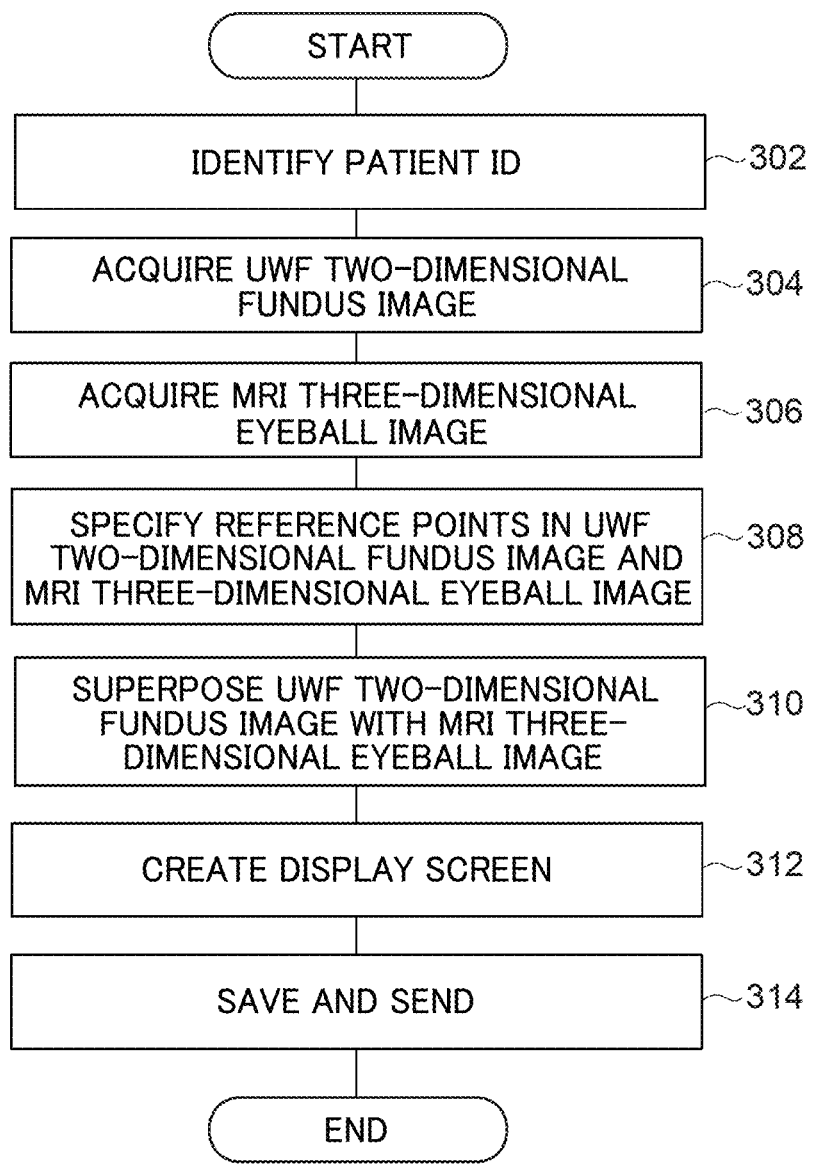
FIG. 6 is a flowchart of an image processing program executed by the management server 140.

Structures of the management server 140 are described with reference to FIG. 3. As shown in FIG. 3, the management server 140 is provided with a control unit 160 and a display/operation unit 170. The control unit 160 is equipped with a computer including the CPU 162, a memory device that is the memory 164, a communications interface (I/F) 166 and so forth. An image processing program, which is depicted in FIG. 6, is memorized in the memory 164. The display/operation unit 170 is a graphical user interface that displays images and accepts various instructions. The display/operation unit 170 is provided with a display 172 and a touch panel 174.

The control unit 160 is an example of a computer program product of the technology of the present disclosure.

The memory 164 is an example of a memory of the technology of the present disclosure. The CPU 162 is an example of a processor of the technology of the present disclosure. The image processing program is an example of a program of the technology of the present disclosure.

Figure 4:
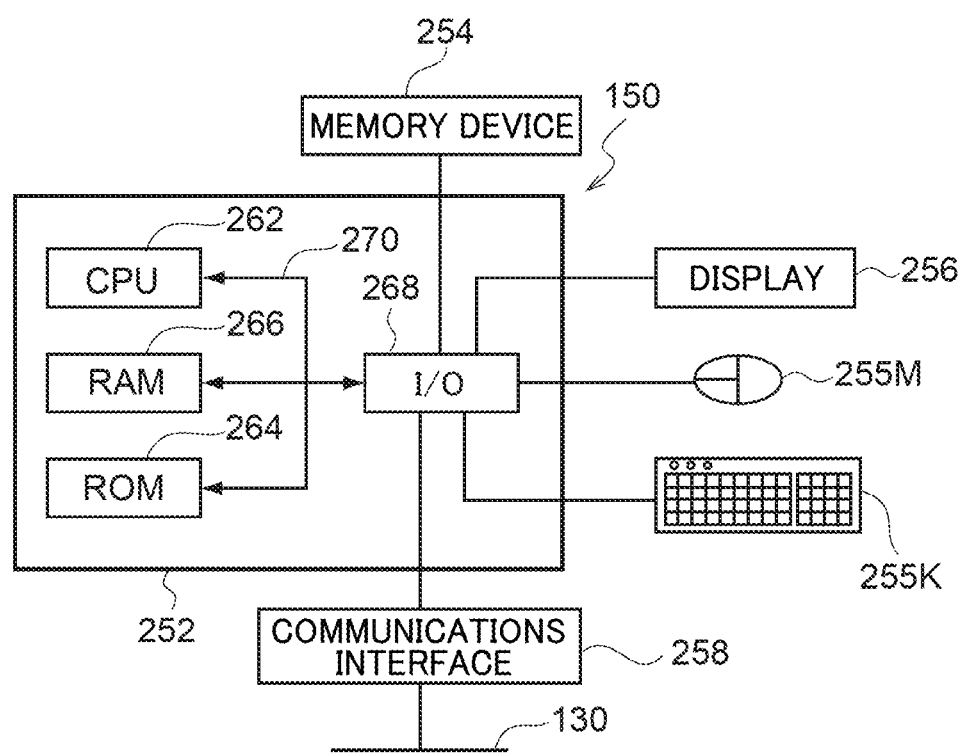
FIG. 4 is a block diagram showing structures of an electronic system of an image viewer 150.

Structures of an electronic system of the image viewer 150 are described with reference to FIG. 4. As shown in FIG. 4, the image viewer 150 is equipped with a computer body 252.

The computer body 252 includes a CPU 262, RAM 266, ROM 264 and an input/output port 268, which are connected to one another via a bus 270. A memory device 254, a display 256, a mouse 255M, a keyboard 255K and a communications interface 258 are connected to the input/output (I/O) port 268. The memory device 254 is structured by, for example, non-volatile memory. The input/output port 268 is connected to the network 130 via the communications interface 258. Thus, the image viewer 150 is capable of communications with the UWF ophthalmology device 110 and the management server 140. The memory device 254 memorizes a data creation program, which is described below.

Figure 5:
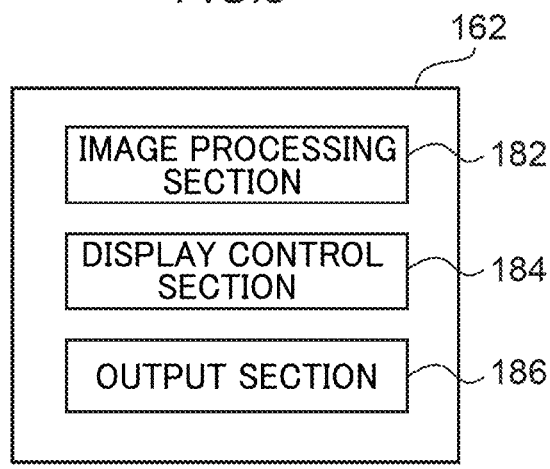
FIG. 5 is a functional block diagram of a CPU 162 of the management server 140.

As shown in FIG. 5, the CPU 162 of the management server 140 functions as the image processing section 182, a display control section 184 and an output section 186.

The image processing section 182 is an example of an acquisition section, a specification section and a generation section of the technology of the present disclosure.

Now, details of image processing by the management server 140 are described using FIG. 6. The CPU 162 of the management server 140 implements the image processing (image processing method) depicted in the flowchart of FIG. 6 by executing the image processing program. The image processing program starts when a start instruction is given by an operator via the touch panel 174.

When instructing the image processing program to start, the operator enters a patient ID via the touch panel 174.

In step 302, the image processing section 182 identifies the patient ID entered via the touch panel 174.

As mentioned above, a UWF two-dimensional fundus image, OCT image and MRI three-dimensional eyeball image are associated and memorized in the memory 164 in association with the patient ID. The UWF two-dimensional fundus image is an image imaging blood vessels in the posterior pole portion and the surrounding area of the fundus, that is, an image visualizing blood vessels of the fundus. The UWF two-dimensional fundus image is an image visualizing blood vessels in the retina and/or the choroid. Because the UWF two-dimensional fundus image includes the surrounding area, the UWF two-dimensional fundus image includes an image of a vortex vein.

The UWF two-dimensional fundus image is an example of a two-dimensional image of the technology of the present disclosure. The MRI three-dimensional eyeball image is an example of a three-dimensional image of the technology of the present disclosure.

In step 304, the image processing section 182 acquires the UWF two-dimensional fundus image memorized in association with the identified patient ID from the memory 164. In step 306, the image processing section 182 acquires the MRI three-dimensional eyeball image memorized in association with the identified patient ID from the memory 164. The sequence of execution of step 304 and step 306 is not limited thus and may be reversed. In either of step 304 and step 306, the image processing section 182 acquires the OCT image.

In step 308, the image processing section 182 specifies mutually corresponding reference points in the UWF two-dimensional fundus image and the MRI three-dimensional eyeball image. For example, a reference point is a structural feature at the fundus of the subject eye that is imaged in both images. Therefore, the reference point is a structural feature that appears in both the UWF two-dimensional fundus image and the MRI three-dimensional eyeball image. A single reference point or plural reference points may be specified. When plural reference points are to be specified, the positions of plural structural features located at different positions from one another in one of the UWF two-dimensional fundus image and the MRI three-dimensional eyeball image are respectively specified as reference points. Plural reference points corresponding to the plural structural features specified as plural reference points in the UWF two-dimensional fundus image are then specified in the other image. Structural features that may be mentioned include, firstly, anatomical features of the subject eye such as the optic disc, the pupil, the macula and so forth, secondly, blood vessel structures such as vortex veins and the like and, thirdly, uneven fundus depression structures manifested by uveitis and the like.

In this exemplary embodiment, the plural reference points are set as a first structural feature and a second structural feature that is disposed at a different position from the first structural feature. The first structural feature and second structural feature are selected from, for example, the optic disc, the pupil and the macula. As an example, the first structural feature is the optic disc and the second structural feature is the macula. It is sufficient that the plural number of reference points is at least two; the plural number may be, for example, three or four or five. The plural reference points may be set as a first structural feature, a second structural feature that is disposed at a different position from the first structural feature, and a third structural feature that is disposed at a different position from the first structural feature and the second structural feature. As an example, the first structural feature is the optic disc, the second structural feature is the macula and the third structural feature is the pupil. In this case, the optic disc that is the first structural feature is specified as a first reference point in the MRI three-dimensional eyeball image and specified as a second reference point in the UWF two-dimensional fundus image. The macula that is the second structural feature is specified as a secondary first reference point in the MM three-dimensional eyeball image and specified as a secondary second reference point in the UWF two-dimensional fundus image. The pupil that is the third structural feature is specified as a tertiary first reference point in the MRI three-dimensional eyeball image and specified as a tertiary second reference point in the UWF two-dimensional fundus image.

Procedures for specifying the plural reference points in the UWF two-dimensional fundus image and the MRI three-dimensional eyeball image include a first procedure and a second procedure. In the first procedure, the plural reference points are first specified in one of the UWF two-dimensional fundus image and the MRI three-dimensional eyeball image and then points that correspond with the specified plural reference points are specified in the other of the UWF two-dimensional fundus image and the MRI three-dimensional eyeball image. In the second procedure, the plural reference points are specified respectively separately in the UWF two-dimensional fundus image and the MRI three-dimensional eyeball image. In the second procedure, a sequence in which the plural reference points are specified may be to first specify the reference points in the UWF two-dimensional fundus image and then specify the reference points in the MRI three-dimensional eyeball image, and may be the reverse sequence.

Figure 7:
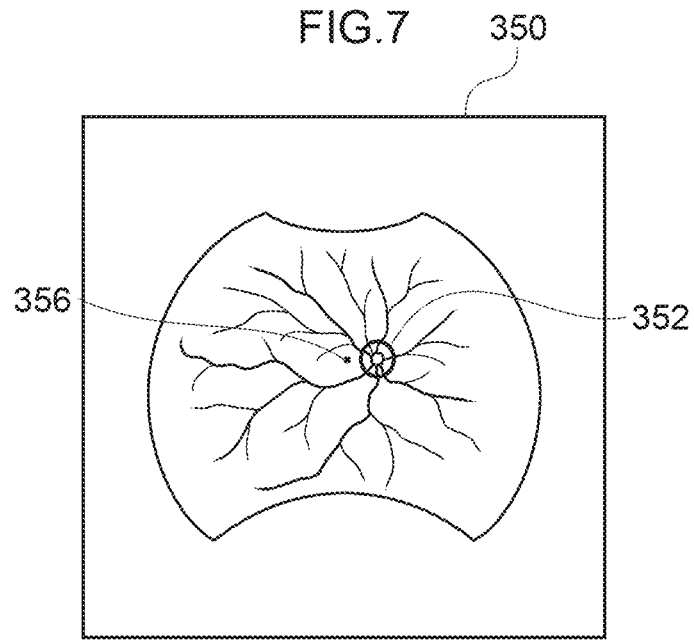
FIG. 7 is a view depicting a situation in which an optic disc 352 and a macula 356 are detected in a UWF two-dimensional fundus image 350.

Firstly, the first procedure is described. As illustrated in FIG. 7, the image processing section 182 detects the optic disc 352 by detecting a brightest point in the UWF two-dimensional fundus image 350. The image processing section 182 detects the macula 356 by detecting a darkest point in the UWF two-dimensional fundus image 350.

Figure 8:
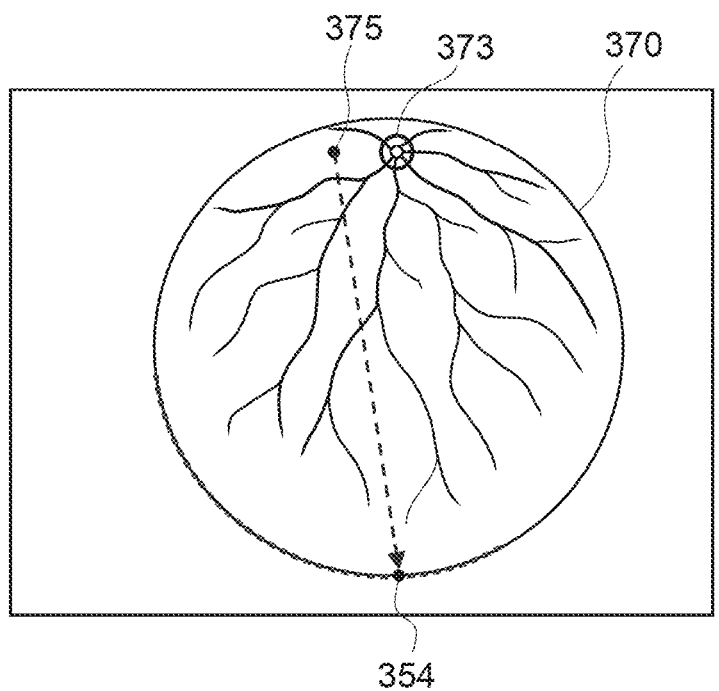
FIG. 8 is a view depicting a situation in which the optic disc 352, the macula 356 and a pupil 354 are detected in the UWF two-dimensional fundus image 350.

Then, as illustrated in FIG. 8, the image processing section 182 detects points in the MRI three-dimensional eyeball image 370 respectively corresponding with the optic disc 352 and macula 356 detected in the UWF two-dimensional fundus image 350. Methods of this detection are described below.

For example, the image processing section 182 first projects the UWF two-dimensional fundus image 350 onto a three-dimensional imaginary spherical surface in accordance with relational expressions of a stereo image projection method. As a result, a spherical surface image on which the UWF two-dimensional fundus image 350 is projected is obtained. In this image, the image processing section 182 disposes the position of the optic disc at, for example, a north pole of the three-dimensional imaginary spherical surface. The image processing section 182 then calculates latitude and longitude coordinates of the macula in the three-dimensional imaginary spherical surface.

The image processing section 182 detects the position of the optic disc 373 in the MRI three-dimensional eyeball image 370. More specifically, the image processing section 182 analyzes the three-dimensional volume image using a three-dimensional shape of the optic disc area that is specified in advance, and detects a three-dimensional shape in the MM three-dimensional eyeball image 370 that corresponds with the three-dimensional shape as being the optic disc area. The image processing section 182 converts the optic disc area to a binary image, applies thinning processing to calculate a central axis thereof, and calculates a region of intersection of the central axis with the MRI three-dimensional eyeball image to be the position of the optic disc 373. The image processing section 182 sets the position of the optic disc 373 as the north pole of the MRI three-dimensional eyeball image 370. The image processing section 182 detects, in the MRI three-dimensional eyeball image 370, the latitude and longitude position calculated for the spherical image in which the UWF two-dimensional fundus image 350 is projected, and sets this detected position as the position of a macula 375.

The technology of the present disclosure is not limited to employing the method as described above of detecting the optic disc 352 and macula 356 in the UWF two-dimensional fundus image 350 and subsequently detecting respective points in the MRI three-dimensional eyeball image 370 that correspond with the optic disc 352 and macula 356. A reverse method may be employed; that is, the optic disc 373 and macula 375 may be detected in the MRI three-dimensional eyeball image 370 and subsequently respective positions corresponding with the optic disc 373 and macula 375 may be detected in the UWF two-dimensional fundus image 350.

Figure 9:
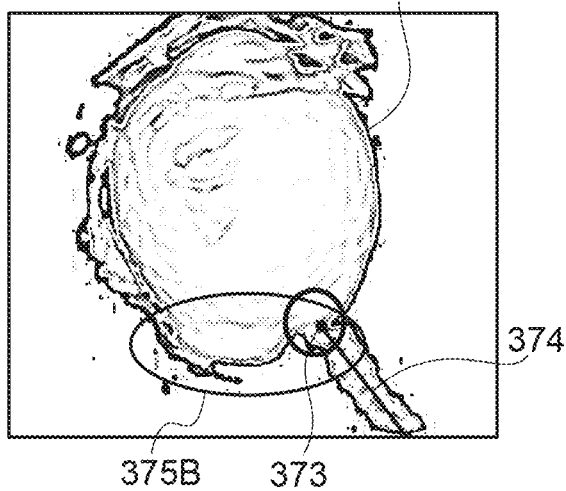
FIG. 9 is a view depicting a situation in which an optic disc 373 is detected in an MRI three-dimensional eyeball image 370.
Figure 10:
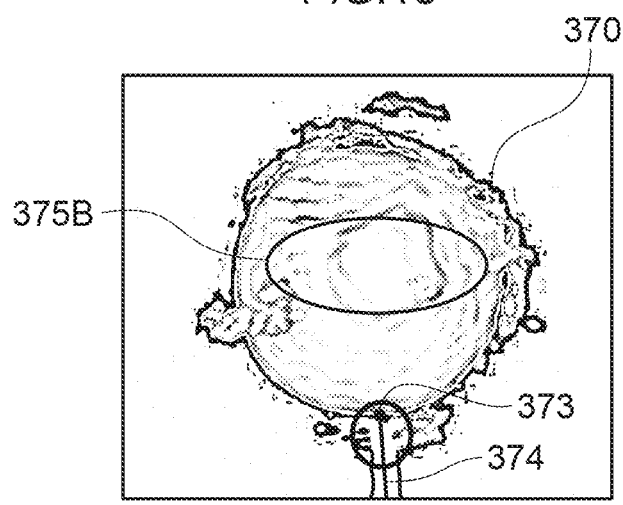
FIG. 10 is a view depicting a situation in which the optic disc 373 is detected in the MM three-dimensional eyeball image 370.

More specifically, as illustrated in FIG. 9 and FIG. 10, the image processing section 182 analyzes a three-dimensional volume image using three-dimensional shapes of the optic nerve path and the eyeball that are specified in advance, and extracts three-dimensional shapes in the MRI three-dimensional eyeball image 370 that correspond with the three-dimensional shapes. The extracted three-dimensional shapes represent an optic nerve path 374 and the eyeball surface. The image processing section 182 detects an intersection point between the optic nerve path 374 and the eyeball as being the optic disc 373.

The image processing section 182 analyzes the three-dimensional volume image using a three-dimensional shape of the optic retina that is specified in advance, and extracts a three-dimensional shape in the MRI three-dimensional eyeball image 370 that corresponds with the three-dimensional shape. The extracted three-dimensional shape represents the retina. The image processing section 182 detects the macula by detecting a central portion of the retina, in accordance with the macula generally being disposed at the center of the retina.

Then, the image processing section 182 detects points in the UWF two-dimensional fundus image 350 respectively corresponding with the optic disc 373 and the macula that have been extracted from the MRI three-dimensional eyeball image 370. More specifically, the image processing section 182 detects the optic disc 352 in the UWF two-dimensional fundus image 350 and projects the UWF two-dimensional fundus image 350 onto a spherical surface in accordance with the relational expressions of the stereo image projection method. In this projection, the image processing section 182 disposes the position of the optic disc at, for example, the north pole of the spherical surface. The image processing section 182 applies positional relationships of the respective corresponding points of the optic disc 373 and macula extracted from the MRI three-dimensional eyeball image 370 to the spherical surface, thus detecting a position of the macula on the spherical surface. The image processing section 182 uses inverse relational expressions of the relational expressions of the stereo image projection method to detect a position in the UWF two-dimensional fundus image 350 that corresponds to the detected position of the macula on the spherical surface.

A method for detecting the optic disc in the MRI three-dimensional eyeball image 370 may, similarly to the method of detecting the optic disc 352 in the UWF two-dimensional fundus image 350, utilize brightnesses in the MRI three-dimensional eyeball image 370.

Now, the second procedure is described. The image processing section 182 detects the optic disc 352 and macula 356 in the UWF two-dimensional fundus image 350 and detects the position of the optic disc in the MRI three-dimensional eyeball image by the methods described for the first procedure. The image processing section 182 sets the tip of an eyeball protrusion in the MRI three-dimensional eyeball image as the position of the corneal center, and detects a point at the opposite pole of the MRI three-dimensional eyeball image as being the macula.

Now, a method for detecting the pupil to be a reference point in the MM three-dimensional eyeball image 370 is described.

As illustrated in FIG. 8, the image processing section 182 detects the macula 375 and the eyeball center in the MRI three-dimensional eyeball image 370. More specifically, the image processing section 182 computes a sphere inscribing the MRI three-dimensional eyeball image 370 and finds the eyeball center by a method of calculating a center of gravity or the like. Then, the image processing section 182 detects the pupil 354 by detecting a point at the opposite side of the eyeball center from the macula 375.

Figure 11A:
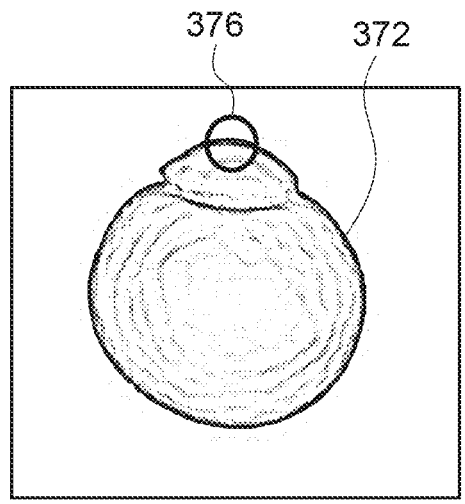
FIG. 11A is a view depicting a situation in which a corneal center 376 is detected in the MRI three-dimensional eyeball image 370.
Figure 11B:
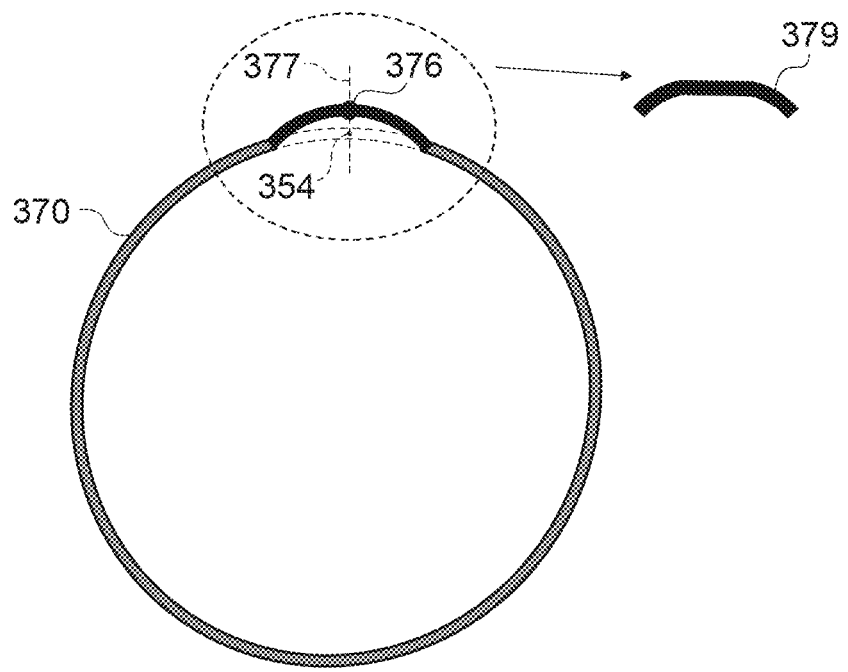
FIG. 11B is a view depicting a situation in which the corneal center 376 and a pupil 378 are detected in the MRI three-dimensional eyeball image 370.

Alternatively, as illustrated in FIG. 11A and FIG. 11B, the image processing section 182 detects a portion that locally protrudes furthest as being the corneal center 376. Usually, the position of the corneal center 376 in the MRI three-dimensional eyeball image 370 (a three-dimensional spherical surface image) may be detected as the tip of a protruding structural portion with a smaller radius of curvature than the vitreous body. Then, the image processing section 182 extrapolates an imaginary surface tangential to the crystalline lens from the MRI three-dimensional eyeball image 370, and sets a point of intersection between the imaginary surface and a perpendicular line 377 from the corneal center 376 as being the pupil 354. The tip of the cornea may not be disposed at the corneal center, such as when the shape of a cornea 379 is flattened by corneal surgery or the like, when the cornea shape is abnormal due to irregular astigmatism, keratoconus or the like, and so forth. In these cases, the shape of the cornea if the cornea were normal may be estimated from the provided MRI three-dimensional eyeball image 370 and an imaginary cornea tip may be specified, or a center point of a flat area of the cornea may be specified as the corneal center.

A staphyloma 375B or the like might be detected as a protrusion corresponding to the cornea in the MRI three-dimensional eyeball image 370 (see FIG. 9 and FIG. 10). However, the staphyloma 375B and the pupil 354 (see FIG. 8) differ in the curvature of curved surfaces thereof. Accordingly, after the image processing section 182 detects protrusions, the image processing section 182 may calculate respective curvatures of the curved surfaces of the protrusions, set a region with greater curvature than a predetermined threshold as being the staphyloma 375B, and eliminate that region as the cornea. Moreover, coordinates at which the staphyloma 375B and the pupil 354 are disposed in the MRI three-dimensional eyeball image 370 are different. Accordingly, after detecting protrusion portions, the image processing section 182 may specify three-dimensional coordinates of the respective protrusion portions, identify the staphyloma 375B from relative positional relationships with other structural features such as the macula, the optic disc and so forth, and eliminate a protrusion that is identified as the staphyloma 375B.

Figure 12:
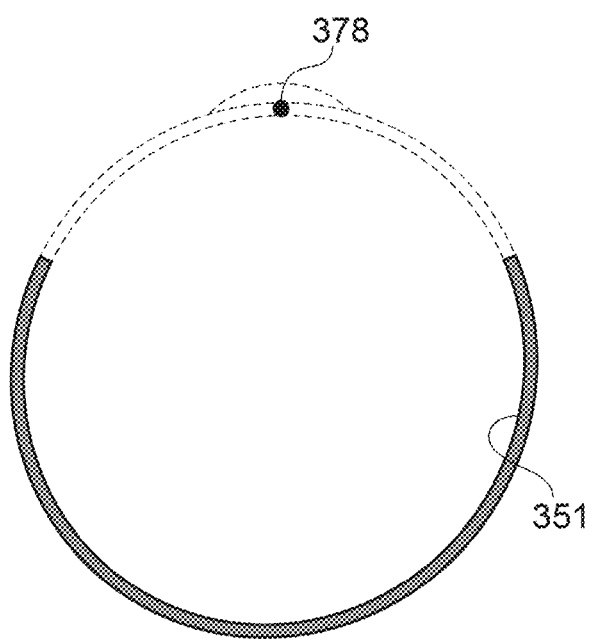
FIG. 12 is a view depicting a situation in which the pupil is not present in the UWF two-dimensional fundus image 350 that images the fundus 351.

Now, a method of detecting the pupil as a reference point in the UWF two-dimensional fundus image 350 is described. As illustrated in FIG. 12, the pupil is not present in the UWF two-dimensional fundus image 350 obtained by imaging the fundus 351. Accordingly, the UWF two-dimensional fundus image 350 is projected onto a spherical surface in accordance with the relational expressions of the stereo image projection method, and the position of a pupil 378 is set to the position of a point at the polar opposite side of the eyeball center from the macula. Alternatively, the position of the pupil is found by extrapolating a spherical surface approximating the projection of the UWF two-dimensional fundus image 350 onto the spherical surface in accordance with the relational expressions of the stereo image projection method.

The pupil position in the UWF two-dimensional fundus image 350 and the position of the pupil 354 in the MRI three-dimensional eyeball image 370 are coordinated using latitude and longitude information on the two spherical surfaces thereof. The position of the pupil may be employed as a reference point for position matching.

A vortex vein may also be a reference point. The vortex vein is disposed in the surrounding area of the fundus. When a two-dimensional image of the subject eye is a UWF fundus image, the image includes the surrounding area of the fundus; therefore, the vortex vein is imaged. To detect a vortex vein in the UWF two-dimensional fundus image, the image processing section 182 first detects blood vessels. Then, the image processing section 182 detects blood veins in a radiating pattern and detects a central position of the radiating pattern as being the vortex vein. The UWF two-dimensional fundus image is an image visualizing the vortex vein.

The contents recited in International Publication (WO) No. 2019/203309 are incorporated by reference into the present specification to the same extent as if specifically and individually recited as being incorporated by reference.

In the MRI three-dimensional eyeball image, the vortex vein may be identified by identifying a drainage path at which choroidal veins flow out of the eye. To detect the vortex vein, the image processing section 182 may analyze the MRI three-dimensional eyeball image and detect an area in which blood vessels are concentrated as the vortex vein. More specifically, the image processing section 182 may detect a blood vessel concentration structure in the vicinity of the equator of the MRI three-dimensional eyeball image (a three-dimensional surface spherical image) as being the position of the vortex vein. A method for detecting this position may be to convert the three-dimensional structural region of the blood vessel concentration structure to a binary image, apply thinning processing to calculate a central axis thereof, and find a region of intersection between the central axis and the MRI three-dimensional eyeball image (the three-dimensional surface spherical image).

When a three-dimensional image is not an MRI image but an OCT volume image, a region in which blood vessels are concentrated may be detected as being a vortex vein.

Figure 13A:
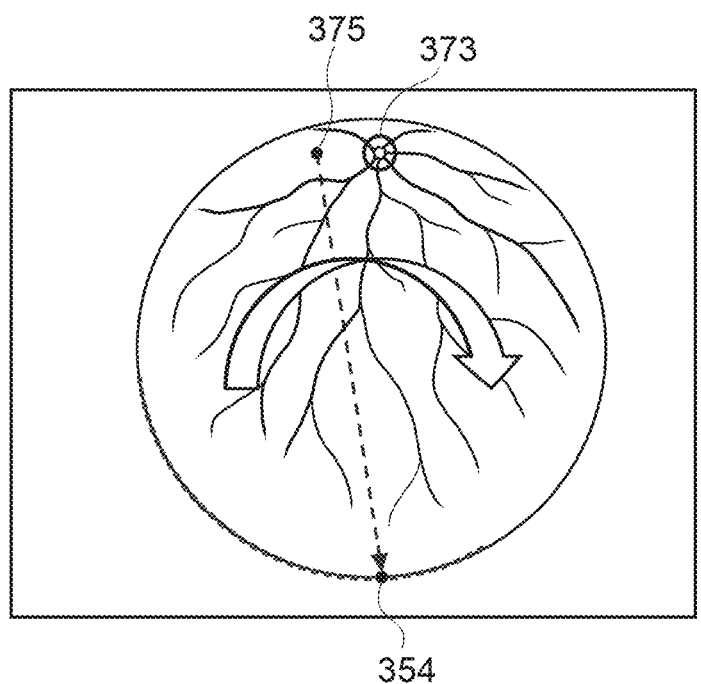
FIG. 13A is a view depicting a situation in which a UWF two-dimensional fundus image is to be superposed with an MRI three-dimensional eyeball image.

In step 310, as illustrated in FIG. 13A, the image processing section 182 coordinates the reference points appearing in both the UWF two-dimensional fundus image and the MRI three-dimensional eyeball image, and superposes the UWF two-dimensional fundus image with at least a portion, for example, the whole, of the MRI three-dimensional eyeball image. It is desirable if a minimum number of the reference points is at least two, as mentioned above.

Figure 13B:
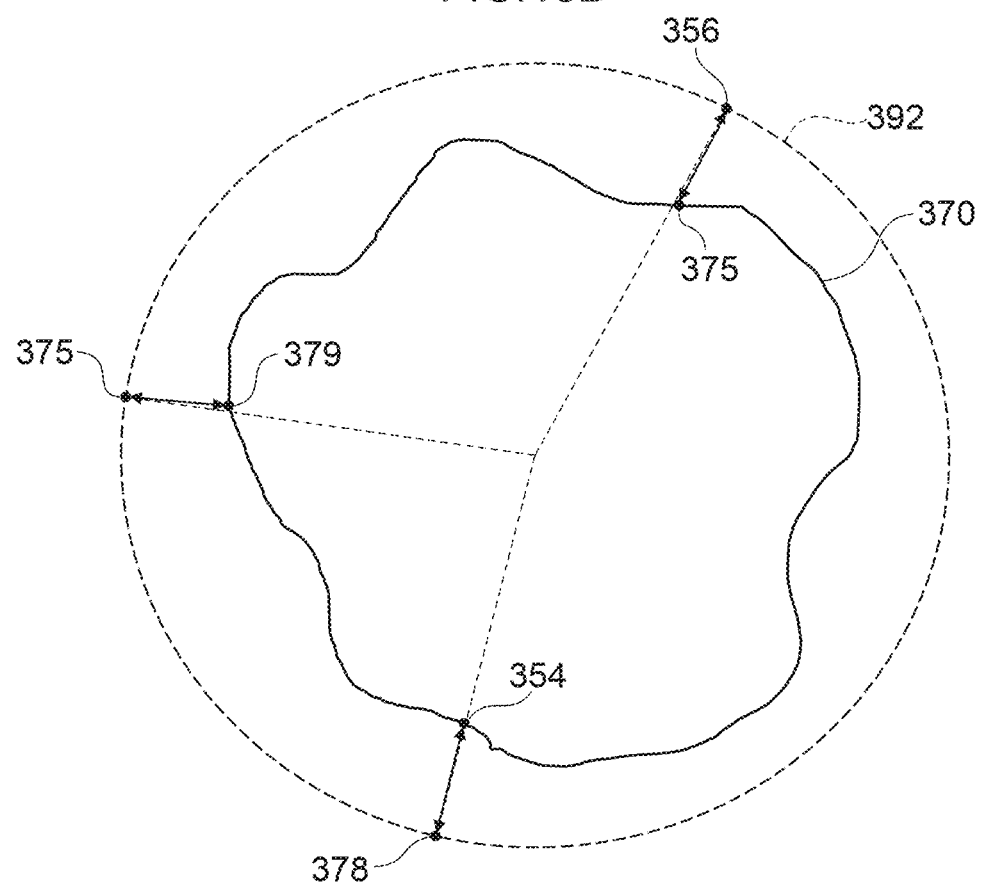
FIG. 13B is a view describing a situation in which the UWF two-dimensional fundus image 350 is superposed.

More specifically, as described above, the image processing section 182 first stereo-projects the UWF two-dimensional fundus image onto a three-dimensional imaginary spherical surface 392 as illustrated in FIG. 13B. The three-dimensional imaginary spherical surface 392 is, for example, a sphere with a diameter of 24 mm. In the example shown in FIG. 13B, the macula 356, the pupil 378 and a vortex vein 357 are detected.

Then, the plural reference points in each of the UWF two-dimensional fundus image and the MRI three-dimensional eyeball image—for example, the macula 356 and 375, the pupil 378 and 354, and the vortex vein 357 and 379—are used to coordinate respective relative positions in the three-dimensional imaginary spherical surface 392 on which the UWF two-dimensional fundus image is projected and the MRI three-dimensional eyeball image 370. More specifically, the image processing section 182 coordinates latitudes and longitudes of the three-dimensional imaginary spherical surface with latitudes and longitudes of the MRI three-dimensional eyeball image. In FIG. 13B, the eyeball surface of the MRI three-dimensional eyeball image 370 is emphasized.

Then, the image processing section 182 superposes the UWF two-dimensional fundus image with the MRI three-dimensional eyeball image such that points in the three-dimensional imaginary spherical surface 392 on which the UWF two-dimensional fundus image is projected correspond with those points in the MRI three-dimensional eyeball image 370. That is, the image processing section 182 uses information relating to positional coordinates of pixels located at the eyeball surface of the MRI three-dimensional eyeball image 370 to re-project points of the UWF two-dimensional fundus image projected onto the three-dimensional imaginary spherical surface 392 at correct positions. More specifically, the image processing section 182 searches for a point in the MRI three-dimensional eyeball image with the same latitude and longitude as that each point in the UWF two-dimensional fundus image, and projects a pixel at that point in the UWF two-dimensional fundus image onto the point that is found. This is carried out for all points of the UWF two-dimensional fundus image.

Information required for the above processing in step 310 to coordinate the respective relative positions in the three-dimensional imaginary spherical surface and the MM three-dimensional eyeball image is information of latitudes and longitudes on the three-dimensional imaginary spherical surface and the MRI three-dimensional eyeball image. Information on lengths, sizes and scale is not necessarily required. Therefore, respective lengths in the three-dimensional imaginary spherical surface and the MRI three-dimensional eyeball image may be different from one another. For example, a distance between the macula 356 and the pupil 354 may be different in the three-dimensional imaginary spherical surface and the MRI three-dimensional eyeball image. However, a value of eye axial length measured by an eye axial length measurement, an equatorial diameter measured by ultrasonic equipment and the like may be used for setting the three-dimensional imaginary spherical surface and the MRI three-dimensional eyeball image to the same size.

In step 312, the display control section 184 creates the display screen 400 displaying information, images and the like, which are described below, for the graphical user interface (GUI).

In step 314, the output section 186 outputs data of the display screen 400. More specifically, the display control section 184 memorizes the data in association with the patient ID in the memory 164 and the output section 186 sends the data to the image viewer 150 together with the patient ID.

When step 314 is complete, the image processing program ends.

Now, the display screen 400 is described with reference to FIG. 14. As shown in FIG. 14, the display screen 400 includes an information area 402 and an image display area 404. The information area 402 includes a patient ID display field 406, a patient name display field 408, an age display field 410, a visual acuity display field 412, a right or left eye display field 414 and an eye axial length display field 416. The image viewer 150 displays corresponding information based on information received from the management server 140 in each display field from the patient ID display field 406 to the eye axial length display field 416.

The layout of the image display area 404 is a layout of images with relevance to an ophthalmologist, and is described more specifically below.

The image display area 404 includes a first section 420 for displaying a UWF two-dimensional fundus image, and a second section 422 for displaying an image in which the UWF two-dimensional fundus image is superposed with an MRI three-dimensional eyeball image.

The image displayed in the second section 422 in which the UWF two-dimensional fundus image is superposed with the MRI three-dimensional eyeball image is, for example, rotatable by reference to the eyeball center in accordance with operations by an operating staff member.

The image display area 404 includes a third section 424, a fourth section 426 and a fifth section 428. The third section 424 displays a posterior eye part tomographic image based on the UWF two-dimensional fundus image and an OCT tomographic image. The fourth section 426 displays an OCT tomographic image of the fundus. The fifth section 428 displays a panorama image (that is, a two-dimensional elevation image) of the en-face of the choroid (a surface perpendicular to the optical axis of measurement by the OCT).

The image display area 404 includes a sixth section 430 for displaying comments.

In the present exemplary embodiment as described above, an image is generated in which a UWF two-dimensional fundus image is superposed with an MRI three-dimensional eyeball image. Thus, an image may be generated with which conditions of the fundus such as, for example, conditions of blood vessels and vortex veins of the fundus may be perceived in three dimensions. This is useful for ophthalmological examinations. Hence, ophthalmologists may conduct highly accurate diagnoses and disease evaluations.

For example, because the UWF two-dimensional fundus image is superposed with the MRI three-dimensional eyeball image, in an examination for strabismus, relevant retinal disease conditions associated with strabismus may be examined.

Because the UWF two-dimensional fundus image is acquired by imaging the fundus through a wide-angle optical system, conditions in a region larger than the fundus may be perceived in three dimensions.

Now, variant examples of the present exemplary embodiment are described.

Figure 15:
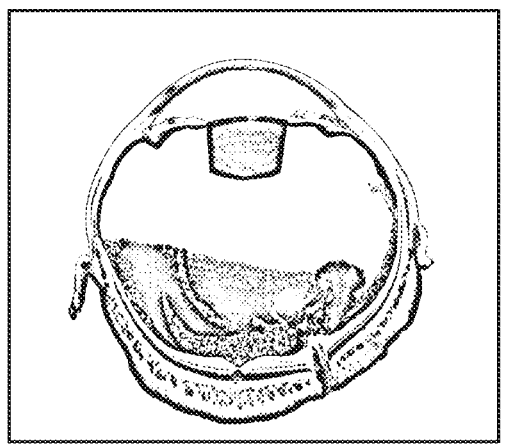
FIG. 15 is a view depicting a situation in which a superposed image, in which a UWF two-dimensional fundus image is superposed with an MRI three-dimensional eyeball image, is superposed with an OCT tomography image of a whole subject eye, which includes an anterior eye part OCT image and a posterior eye part OCT image.

A first variant example is described. In the exemplary embodiment described above, an image in which a UWF two-dimensional fundus image is superposed with an MM three-dimensional eyeball image is displayed in the second section 422 of the image display area 404 of the display screen 400 in FIG. 14, but the technology of the present disclosure is not limited thus. For example, as shown in FIG. 15, a superposed image in which a UWF two-dimensional fundus image is superposed with an MRI three-dimensional eyeball image may be superposed with an OCT tomographic image of the whole subject eye including the anterior eye part and the posterior eye part. Conditions of the fundus may be perceived three-dimensionally in relation to conditions in tomography.

Figure 16:
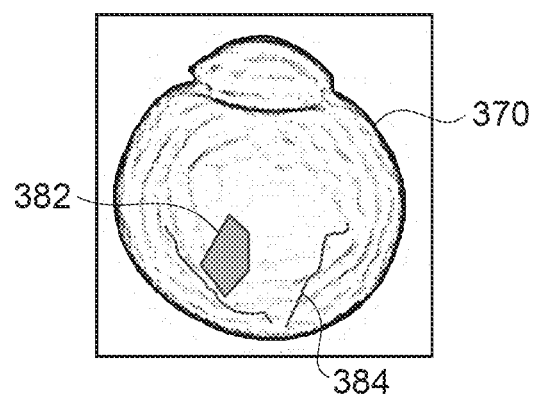
FIG. 16 is a view depicting a situation in which images 382 and 384 of partial regions of a fundus image are superposed with the MRI three-dimensional eyeball image 370.

A second variant example is described. In the exemplary embodiment described above, an image in which the whole of a UWF two-dimensional fundus image is superposed with an MRI three-dimensional eyeball image is displayed in the second section 422 in FIG. 14, but the technology of the present disclosure is not limited thus. For example, as shown in FIG. 16, the UWF two-dimensional fundus image to be superposed with the MRI three-dimensional eyeball image 370 is partial region images 382 and 384 of the UWF two-dimensional fundus image. The partial regions may be, for example, images in which portions of the two-dimensional image are cropped out, may be images of lesion areas, and may be fundus blood vessel images in which blood vessels alone are extracted from a fundus image.

An image of a lesion area is, for example, an image in which the fundus image is cropped to a region identified by a physician or an artificial intelligence. An example of a lesion area is a retinal detachment area. The image 382 of a retinal detachment area is displayed, for example, with green coloring. The image 384 of a blood vessel region is displayed, for example, with red coloring. The MRI three-dimensional eyeball image 370 is displayed semi-transparently. Either of the image of the lesion area and the image of the blood vessel region may be displayed selectively and successively. Thus, only the image of the lesion area is displayed or only the image of the blood vessel region is displayed on the MRI three-dimensional eyeball image 370 that is displayed semi-transparently.

A third variant example is described. In the memory 164 as described above, a UWF two-dimensional fundus image and an MRI three-dimensional eyeball image are associated and memorized in association with a patient ID, but the technology of the present disclosure is not limited thus. For example, a UWF two-dimensional fundus image, a posterior eye part OCT image and an anterior eye part OCT image may be associated and memorized in the memory 164 in association with a patient ID. In step 304, the image processing section 182 acquires the UWF two-dimensional fundus image, posterior eye part OCT image and anterior eye part OCT memorized in association with the patient ID from the memory 164.

In step 310, the image processing section 182 generates a first superposed image in which the UWF two-dimensional fundus image is superposed with at least a portion of an MRI three-dimensional eyeball image, and generates a second superposed image in which the first superposed image is superposed with the posterior eye part OCT image. The second section 422 displays the first superposed image and the second superposed image. Shape data of the posterior eye part of the subject eye may be acquired from the posterior eye part OCT image, and image processing may be performed on the basis of the shape data to, for example, deform the first superposed image so as to correspond with the shape of the posterior eye part of the subject eye.

Alternatively in step 310, the image processing section 182 generates an image in which a superposed image, in which the UWF two-dimensional fundus image is superposed with the MRI three-dimensional eyeball image, is superposed with the anterior eye part OCT image. The second section displays the image in which the superposed image superposing the UWF two-dimensional fundus image on the at least a portion of the MRI three-dimensional eyeball image is superposed on the anterior eye part OCT image. Shape data of the cornea of the subject eye may be acquired from the anterior eye part OCT image, and image processing may be performed to, for example, deform the superposed image on the basis of the shape data.

A fourth variant example is described. A two-dimensional image memorized in association with the patient ID in the memory 164 as described above is a single two-dimensional image obtained at a certain time, but the technology of the present disclosure is not limited thus. For example, the memory 164 may memorize plural subject eye fundus images in association with the patient ID as two-dimensional images, including a first subject eye fundus image and a second subject eye fundus image obtained by imaging the fundus at a different time from the first subject eye fundus image. A predetermined event occurs between the time at which the first subject eye image is obtained and the time at which the second subject eye image is obtained. The predetermined event is, for example, surgery on the subject eye. Below, as an example, a situation is described in which the two-dimensional images are a first UWF two-dimensional fundus image and a second UWF two-dimensional fundus image.

The first UWF two-dimensional fundus image and second UWF two-dimensional fundus image are examples of a first two-dimensional image and a second two-dimensional image of the technology of the present disclosure.

In step 304, the image processing section 182 acquires a first UWF two-dimensional fundus image and second UWF two-dimensional fundus image associated with the patient ID from the memory 164.

In step 310, the image processing section 182 superposes the first UWF two-dimensional fundus image and second UWF two-dimensional fundus image with the MRI three-dimensional eyeball image. Here, the image processing section 182 may superpose differences between the first UWF two-dimensional fundus image and the second UWF two-dimensional fundus image with the MRI three-dimensional eyeball image. Alternatively, the image processing section 182 may superpose both the first UWF two-dimensional fundus image and the second UWF two-dimensional fundus image with the MRI three-dimensional eyeball image, and may extract differences between the first UWF two-dimensional fundus image and second UWF two-dimensional fundus image superposed with the MRI three-dimensional eyeball image.

Thus, because the first UWF two-dimensional fundus image and second UWF two-dimensional fundus image are superposed with the MRI three-dimensional eyeball image, states of the fundus before and after the surgery on the subject eye may be perceived in three dimensions. Both the image in which differences between the first UWF two-dimensional fundus image and second UWF two-dimensional fundus image are superposed with the MRI three-dimensional eyeball image and the image in which the first UWF two-dimensional fundus image and second UWF two-dimensional fundus image are superposed with the MRI three-dimensional eyeball image may be images of only a predetermined region containing the area of the surgery.

This surgery may be, for example, scleral buckling surgery, that is, a treatment to prevent the advance of rhegmatogenous retinal detachment by pressing the outer side (the sclera) of the eyeball with silicone.

Superposing the first UWF two-dimensional fundus image preceding the surgery with the MRI three-dimensional eyeball image is useful for understanding where the retinal detachment is located as seen from the outer side of the eyeball. Because the second UWF two-dimensional fundus image subsequent to the surgery is superposed with the MRI three-dimensional eyeball image, it may be verified that the silicone is pressing against the retinal detachment area.

Below, a range of further variant examples are described.

In the examples described above, an MRI three-dimensional eyeball image is employed as a three-dimensional image of the subject eye but the technology of the present disclosure is not limited thus. It is sufficient that the three-dimensional image is an image obtained using equipment that generates three-dimensional image data of the subject eye. Three-dimensional images that may be mentioned include, as alternative examples, X-ray CT (computed tomography) three-dimensional eyeball images, ultrasonic three-dimensional eyeball images, OCT images of the whole subject eye (whole-eye OCT images), OCT angiography images of the whole subject eye (OCTA images) and so forth. A three-dimensional image of the subject eye may refer to a three-dimensional image of the subject eye that is obtained using MRI equipment, X-ray CT equipment, ultrasonic imaging equipment, OCT equipment or the like, which is a first device of a first modality (medical imaging and diagnostics equipment) that generates three-dimensional image data of the subject eye. When an X-ray CT three-dimensional eyeball image or an ultrasonic three-dimensional eyeball image is employed as the three-dimensional image, the optic disc, a vortex vein, the pupil and the like may be employed as reference points. When the three-dimensional image of the subject eye is an OCT image including the posterior pole portion, the optic disc and a vortex vein in the image may be employed as reference points. When the three-dimensional image is an OCT image imaging only the posterior pole portion, a position of the pupil estimated from an actual shape display may be employed as a reference point.

Note that the three-dimensional image mentioned above is an image obtained by using equipment (MRI equipment, X-ray CT equipment, ultrasonic imaging equipment, OCT equipment or the like) that generates three-dimensional image data of the subject eye. Therefore, the meaning of this term "three-dimensional image" encompasses images that are not displayed three-dimensionally (stereoscopically). The technology of the present disclosure is not limited thus. For example, the three-dimensional image of the subject eye may be an image that is plotted in a flat plane with a stereoscopic appearance, and that is re-created and mentally perceived as a solid by binocular parallax.

A stereoscopic image that is obtained by applying image processing (segmentation or the like) to a three-dimensional image may be employed as the three-dimensional image of the subject eye. The stereoscopic image of the subject eye is an image that displays at least a portion of the subject eye stereoscopically (three-dimensionally).

In the examples described above, the UWF two-dimensional fundus image is employed as the two-dimensional image of the subject eye to be superposed with the MRI three-dimensional eyeball image, but the technology of the present disclosure is not limited thus. Two-dimensional images that may be mentioned include, as alternative examples, fundus camera images, en-face OCT, en-face OCTA images and the like. The two-dimensional image may be a two-dimensional tomographic image created using OCT volume data, or the like. A fundus image may refer to a two-dimensional image of the subject eye (also referred to as a planar image, an elevation image or the like) that is obtained using SLO equipment, OCT equipment (which generates an en-face image from OCT volume data), a fundus camera or the like, which is a second device of a second modality that generates two-dimensional image data of the subject eye.

It is sufficient that the image of the subject eye to be superposed with the MRI three-dimensional eyeball image is an image obtained by equipment of a different modality from MRI; it need not necessarily be a two-dimensional image. For example, the image to be superposed may be a three-dimensional image such as OCT volume data of the whole subject eye or the like, and may be image data in which time information is attached to a three-dimensional image such as an OCT angiography image of the whole subject eye or the like. When OCT volume data is superposed with the MRI three-dimensional eyeball image, three-dimensional information of the subject eye may be mutually complementary. More specifically, when OCT volume data is superposed with the MRI three-dimensional eyeball image, a three-dimensional image of the subject eye is obtained in which rough information about a region that is not scanned with light by the OCT equipment is provided by the MRI three-dimensional eyeball image and detailed blood vessel information of the region that is scanned with light by the OCT equipment is provided. Even when an OCT volume image is superimposed with an MRI image, a vortex vein, the pupil and the optic disc may be employed as reference points. Similarly, an OCT volume image may be superimposed with a CT image, ultrasonic image or the like of the subject eye.

In the examples described above, the management server 140 executes the image processing program, but the technology of the present disclosure is not limited thus. For example, the image processing program may be executed by any of the UWF ophthalmology device 110, the MRI image acquisition device 120, the image viewer 150, other ophthalmological equipment (test equipment for field of vision measurement, intraocular pressure measurement and the like), and diagnostic support equipment that uses artificial intelligence to perform image analysis.

The OCT unit 20 may be omitted from the UWF ophthalmology device 110, in which case the focus adjustment mechanism 28 and light path combining component 21 of the imaging optical system 19 may also be omitted.

In the present disclosure, there may be only one of each structural element (devices and the like) and there may be two or more, provided no conflicts result.

In the examples described above, examples are described in which image processing is executed by a software configuration using a computer, but the technology of the present disclosure is not limited thus. For example, instead of a software configuration using a computer, the image processing may be executed only by a hardware configuration such as a field programmable gate array (FPGA), application-specific integrated circuit (ASIC) or the like. Some of the image processing may be executed by a software configuration and the rest of the processing may be executed by a hardware configuration.

Thus, the technology of the present disclosure encompasses structures in which the image processing is executed by a software configuration using a computer and structures in which the image processing is not executed by a software configuration. Therefore, the technology of the present disclosure encompasses the following technologies.

—First Technology—

An image processing device including:

an acquisition section that acquires a three-dimensional image of a subject eye and a two-dimensional image of the subject eye;

a specification section that specifies a first reference point in the three-dimensional image and a second reference point in the two-dimensional image; and a generation section that generates an image in which the two-dimensional image is superposed with at least a portion of the three-dimensional image, including coordinating the first reference point in the three-dimensional image with the second reference point in the two-dimensional image.

—Second Technology—

An image processing method including:

an acquisition section acquiring a three-dimensional image of a subject eye and a two-dimensional image of the subject eye;

a specification section specifying a first reference point in the three-dimensional image and a second reference point in the two-dimensional image; and a generation section generating an image in which the two-dimensional image is superposed with at least a portion of the three-dimensional image, including coordinating the first reference point in the three-dimensional image with the second reference point in the two-dimensional image.

The following technology is proposed in accordance with the details disclosed above.

Third Technology—

A computer program product for image processing, the computer program product not being transitory signals but being provided with a computer readable memory medium, and a program being stored on the computer readable memory medium, the program being executed by a computer to execute a subject eye examination method including:

acquiring a three-dimensional image of a subject eye and a two-dimensional image of the subject eye;

specifying a first reference point in the three-dimensional image;

specifying a second reference point in the two-dimensional image;

generating an image in which the two-dimensional image is superposed with at least a portion of the three-dimensional image, including coordinating the first reference point in the three-dimensional image with the second reference point in the two-dimensional image.

The following technology is proposed in accordance with the details disclosed above.

Fourth Technology—

A subject eye examination method including:

acquiring a three-dimensional image of a subject eye and a two-dimensional image of the subject eye;

specifying a first reference point in the three-dimensional image;

specifying a second reference point in the two-dimensional image;

generating an image in which the two-dimensional image is superposed with at least a portion of the three-dimensional image, including coordinating the first reference point in the three-dimensional image with the second reference point in the two-dimensional image; and examining the subject eye on the basis of the image in which the two-dimensional image is superposed with the at least a portion of the three-dimensional image.

The image processing described above is merely an example. Accordingly, it will be clear that unnecessary steps may be removed, new steps may be added and sequences of processing may be rearranged, within a scope not departing from the gist of the disclosure.

All references, patent applications and technical specifications cited in the present specification are incorporated by reference into the present specification to the same extent as if the individual references, patent applications and technical specifications were specifically and individually recited as being incorporated by reference.

What is claimed is:

1. An image processing method comprising:
   acquiring a three-dimensional image of a whole subject eye, including an anterior eye part and a posterior eye part, and a two-dimensional image of the subject eye;
   specifying a first reference point in the three-dimensional image;
   specifying a second reference point in the two-dimensional image;
   generating an image in which the two-dimensional image is superposed with at least a portion of the three-dimensional image, including coordinating the first reference point in the three-dimensional image with the second reference point in the two-dimensional image,
   wherein the two-dimensional image includes a first subject eye image and a second subject eye image, the second subject eye image being obtained by imaging the subject eye at a different time from the first subject eye image,
   wherein generating the superposed image includes generating an image in which the first subject eye image and the second subset eye image are superposed with the three-dimensional image; and
   extracting differences between the first subject eye image and the second subject eye image from the image superposed with the three-dimensional image.

2. The image processing method according to claim 1, further comprising outputting the superposed image.

3. The image processing method according to claim 1, wherein the two-dimensional image superposed with the at least a portion of the three-dimensional image is an image imaging at least a partial region of the fundus.

4. The image processing method according to claim 1, wherein the two-dimensional image superposed with the at least a portion of the three-dimensional image is an image in which blood vessels of the fundus are visualized.

5. The image processing method according to claim 1, wherein the two-dimensional image superposed with the at least a portion of the three-dimensional image is an image in which a vortex vein is visualized.

6. The image processing method according to claim 1, wherein the two-dimensional image is a fundus image obtained by imaging the fundus via a wide-angle optical system.

7. The image processing method according to claim 1, wherein the first reference point and the second reference point include a structural feature that appears in both the three-dimensional image and the two-dimensional image.

8. The image processing method according to claim 1, wherein
a plurality of first reference points disposed at mutually different positions are specified in the three-dimensional image,
a plurality of second reference points disposed at mutually different positions are specified in the two-dimensional image, and
the plurality of second reference points are structural features that correspond respectively with the plurality of first reference points.

9. The image processing method according to claim 1, wherein the first reference point and the second reference point are a position of one of a macula, an optic disc and a pupil.

10. The image processing method according to claim 1, wherein generating the superposed image comprises:
projecting the two-dimensional image onto a three-dimensional imaginary spherical surface; and
superposing the two-dimensional image projected onto the three-dimensional imaginary spherical surface with the three-dimensional image such that the second reference point in the two-dimensional image projected onto the three-dimensional imaginary spherical surface coincides with the first reference point in the three-dimensional image.

11. The image processing method according to claim 1, wherein:
the two-dimensional image includes an SLO image and a posterior eye part OCT image; and
generating the superposed image includes superposing the SLO image and the posterior eye part OCT image with at least portions of the three-dimensional image.

12. The image processing method according to claim 1, wherein:
the two-dimensional image includes a fundus image and an anterior eye part OCT image; and
generating the superposed image includes generating an image in which the fundus image and the anterior eye part OCT image are superposed with at least portions of the three-dimensional image.

13. The image processing method according to claim 1, wherein:
the two-dimensional image includes a fundus image and an OCT image of the whole subject eye; and
generating the superposed image includes generating an image in which the fundus image and the OCT image of the whole subject eye are superposed with at least portions of the three-dimensional image.

14. The image processing method according to claim 1, wherein the two-dimensional image superposed with the three-dimensional image is an image containing a region showing a lesion area.

15. The image processing method according to claim 1, wherein the two-dimensional image superposed with the three-dimensional image represents differences between the first subject eye image and the second subject eye image.

16. The image processing method according to claim 1, wherein the three-dimensional image is an MRI three-dimensional eyeball image.

17. An image processing method comprising:
acquiring a three-dimensional image of a whole subject eye, including an anterior eye part and a posterior eye part, and a two-dimensional image of the subject eye;
specifying a first reference point in the three-dimensional image;
specifying a second reference point in the two-dimensional image; and
generating an image in which the two-dimensional image is superposed with at least a portion of the three-dimensional image, including coordinating the first reference point in the three-dimensional image with the second reference point in the two-dimensional image,
the two-dimensional image of the subject eye includes a plurality of two-dimensional images, the plurality of two-dimensional images including a first two-dimensional image and a second two-dimensional image; and
generating the superposed image includes:
generating a first superposed image in which the first two-dimensional image is superposed with at least a portion of the three-dimensional image, and
generating a second superposed image in which the second two-dimensional image is superposed with at least a portion of the first superposed image.

18. An image processing device comprising memory and a processor connected to the memory, the processor executing an image processing method comprising:
acquiring a three-dimensional image of a whole subject eye, including an anterior eye part and a posterior eye part, and a two-dimensional image of the subject eye;
specifying a first reference point in the three-dimensional image;
specifying a second reference point in the two-dimensional image;
generating an image in which the two-dimensional image is superposed with at least a portion of the three-dimensional image, including coordinating the first reference point in the three-dimensional image with the second reference point in the two-dimensional image,
wherein the two-dimensional image includes a first subject eye image and a second subject eye image, the second subject eye image being obtained by imaging the subject eye at a different time from the first subject eye image,
wherein generating the superposed image includes generating an image in which the first subject eye image and the second subset eye image are superposed with the three-dimensional image; and
extracting differences between the first subject eye image and the second subject eye image from the image superposed with the three-dimensional image.

19. A non-transitory memory medium memorizing a program executable by a computer to execute an image processing method comprising:
acquiring a three-dimensional image of a whole subject eye, including an anterior eye part and a posterior eye part, and a two-dimensional image of a subject eye;
specifying a first reference point in the three-dimensional image;
specifying a second reference point in the two-dimensional image;
generating an image in which the two-dimensional image is superposed with at least a portion of the three-dimensional image, including coordinating the first reference point in the three-dimensional image with the second reference point in the two-dimensional image,
wherein the two-dimensional image includes a first subject eye image and a second subject eye image, the second subject eye image being obtained by imaging the subject eye at a different time from the first subject eye image, wherein generating the superposed image includes generating an image in which the first subject eye image and the second subset eye image are superposed with the three-dimensional image; and extracting differences between the first subject eye image and the second subject eye image from the image superposed with the three-dimensional image.

* * * * *